United States Patent [19]

Arakawa

[11] Patent Number: 4,873,312

[45] Date of Patent: Oct. 10, 1989

[54] METHOD FOR PURIFYING INTERFERON AND COMPOSITION OF MATTER PRODUCED THEREBY

[75] Inventor: Tsutomu Arakawa, Thousand Oaks, Calif.

[73] Assignee: Amgen, Thousand Oaks, Calif.

[21] Appl. No.: 727,147

[22] Filed: Apr. 25, 1985

[51] Int. Cl.$^4$ ...................... C07K 15/26; A61K 45/02
[52] U.S. Cl. .................................... 530/351; 424/85.5
[58] Field of Search ................. 424/85, 85.5; 530/351; 435/69, 811, 351

[56] References Cited

U.S. PATENT DOCUMENTS

| | | | |
|---|---|---|---|
| 4,465,622 | 8/1984 | Nobuhara et al. | 424/85 |
| 4,476,049 | 10/1984 | Kung | 424/85 |
| 4,518,526 | 5/1985 | Olson | 435/68 |
| 4,686,284 | 8/1987 | Nara et al. | 435/811 |

FOREIGN PATENT DOCUMENTS

| | | |
|---|---|---|
| 077670 | 10/1982 | European Pat. Off. |
| 110044 | 9/1983 | European Pat. Off. |
| 140127 | 9/1984 | European Pat. Off. |
| 136694 | 10/1984 | European Pat. Off. |
| WO8304053 | 11/1983 | PCT Int'l Appl. |
| 2138004 | 3/1984 | United Kingdom |

OTHER PUBLICATIONS

Yip et al., Proc. Natl. Acad. Sci., vol. 79, pp. 1820–1824, 1982.
Ichikawa et al., Biochimica et Biophysica Acta, 580, 120–128 (1979).
Le et al., J. Immunol., 132(3), 1300–1304 (1984).
Lee et al., Biochemistry, 18(24), 5518–5526 (1979).
Minton, Biopolymers, 20, 2093–2120 (1981).
Yip et al., Proc. Nat'l Acad. Sci. (U.S.A.), 78(3), 1601–1605 (1981).
Hsu et al., Biochemistry, 24(27), 7959–7963 (1985).
Arakawa et al., J. Biol. Chem., 260(27) 14435–14439 (1985).
Chemical Abstracts, 103, p. 560, Abst. No. 158845j (1985).
Gray et al., Nature, 295, 503–508 (1982).
Devos et al., Nucl. Acids Res., 10, 2487–2501 (1982).

Primary Examiner—Blondel Hazel
Attorney, Agent, or Firm—Marshall, O'Toole, Gerstein, Murray & Bicknell

[57] ABSTRACT

A composition of matter consisting of recombinant human immune interferon having a near-UV circular dichroic spectrum in aqueous solution at neutral pH with positive bands at about 259 nm, 266 nm, 280 nm, and 287 nm, and with shoulders at about 270 nm and 292 nm. Also disclosed is a method for purifying human immune interferon in which proper refolding of the interferon is accomplished by unfolding in a denaturant, such as urea, dilution in ammonium acetate to approximately 0.18 mg/ml of interferon (or less), and dialysis of the solution. The properly folded, purified product which results has a four- to eight-fold greater activity than the aggregate which otherwise results.

2 Claims, 6 Drawing Sheets

METHOD FOR PURIFYING INTERFERON AND COMPOSITION OF MATTER PRODUCED THEREBY

BACKGROUND

The present invention pertains in general to methods for purifying interferon produced by recombinant technology and to the products of the purification, and in particular to methods for purifying human immune interferon and a purified human immune interferon 4A.

The interferons form a family of antiviral and immunoregulatory proteins which are known to be naturally produced by fibroblasts, epithelial cells, and types of white blood cells called macrophages and lymphocytes. The three identified types of interferon are referred to as alpha (leukocyte), beta (fibro-epithelial), and gamma (immune).

All three types of interferon are being investigated for use in the treatment of human diseases. As a result, it is important to highly purify interferon in order to remove contaminants which might lead to side effects such as fever and allergic reactions. Despite the fact that all of the types of interferon presumably have common structural and chemical properties, no single method has been found to be effective in purifying all interferons.

Techniques for purifying interferons include affinity chromatography (controlled pore glass, CPG; zinc chelates; concanavalin A; anti-interferon antibodies; and acrylonitrile high polymers [Nobuhara, et al., U.S. Pat. No. 4,465,622]; and affinity chromatography plus gel filtration chromatography [Yip, et al., *Proc.Natl.Acad.- Sci. USA*, 78: 1601–1605 (1981)]. These techniques have been used to obtain lymphocyte-produced human immune interferon having a specific activity estimated to be about $10^7$ units per milligram of protein. Yip, et al., supra. However, lymphocytes are difficult to culture and the amount of interferon economically producible from cultures of lymphocytes is far less than that producible by means of recombinant technology.

Synthetic and cDNA genes coding for human immune interferon (IFN-γ) have been inserted into plasmid vectors, introduced into procaryotic and eucaryotic hosts, and used to produce recombinant human immune interferons (rIFN-γ) in "mature" and analog forms. "Mature" rIFN-γ has an amino acid sequence of 146 residues, the amino terminal of which begins Cys-Tyr-Cys, based upon determination of the sequence of the gene encoding human immune interferon. Goeddel, et al., European patent application No. 077670. Various analogs of mature rIFN-γ are described in Alton, et al., published PCT patent application No. WO83/04053. Among those described are analogs lacking the amino terminal Cys-Tyr-Cys residues, i.e., [des-$Cys^1$-$Tyr^2$-$Cys^3$] IFN-γ analogs. See also, Alton, et al., in "The Biology of the Interferon System 1983", De Maeyer, et al., eds., pages 119–128, Elsevier Science Publishers (1983), referring to "IFN-γ4" which is [des-$Cys^1$-$Tyr^2$-$Cys^3$-$Lys^{81}$] IFN-γ expressed in $Met^{-1}$ form. As ordinarily directly expressed in *E.coli*, rIFN-γ differs from the natural IFN-γ produced by lymphocytes in having an N-terminal methionine residue and in not being glycosylated. Thus, mature rIFN-γ is directly expressed as [$Met^{-1}$] IFN-γ and the recombinant-produced analog [des-$Cys^1$-$Tyr^2$-$Cys^3$] IFN-γ (hereinafter referred to as "recombinant human immune interferon 4A" or "IFN-γ4A") is expressed as [$Met^{-1}$, des-$Cys^1$-$Tyr^2$-$Cys^3$] IFN-γ.

The native form of IFN-γ is reported to be a 40,000 to 60,000 molecular weight oligomer, which is presumably a dimer of two reported monomeric forms having molecular weights of 20,000 and 25,000. Removal of the carbohydrate moieties of the monomers by glycosidase treatment produces monomers of 16,000 and 18,500 molecular weight, respectively. Le, et al., *J.Immunol.*, 132: 1300–1304 (1984). A monomeric form of rIFN-γ has been calculated to have a molecular weight of 17,140. The differences in molecular weight between natural and recombinant forms IFN-γ may be explained, at least in part, by the fact that natural IFN-γ has undergone processing which has removed C-terminal amino acid residues, while the rIFN-γ contains these additional residues.

Any procedure for the isolation of IFN-γ must take into account the potential instability of IFN-γ upon acid treatment. For example, Yip, et al., supra, observe that natural IFN-γ exhibits an almost ten-fold drop in antiviral activity upon dialysis against a pH 2 solution followed by a neutral phosphate buffer. This suggests that IFN-γ is denatured in acid and does not refold into the native structure.

A further complication in the purification of rIFN-γ is involved with its extraction from *E.coli*. While natural IFN-γ may be harvested from the medium surrounding cultured lymphocytes, *E.coli* rIFN-γ is harvested by breaking open bacterial cells with a consequent release of proteolytic enzymes which may degrade the interferon produced. Denaturants, such as urea and guanidine-HCl, inhibit enzyme activity without irreversible loss in the activity of interferon during extraction. Kung, U.S. Pat. No. 4,476,049.

However, once denatured (unfolded), the appropriate conditions for refolding interferon are not readily determined. Consequently, although one approach to renaturing soluble native protein such as immunoglobulin or methionine-prochymosin involves denaturation and dilution in an alkaline solution of urea or guanidine hydrochloride and renaturation by reducing the pH below a pH effective to denature the protein [see, e.g., Lowe, et al., U.K. patent application No. GB 2138004A], the application of such techniques to interferon is not straightforward.

Consequently, it is desirable to have a method for purifying interferon, particularly rIFN-γ, such that it is provided in highly active forms.

SUMMARY OF THE INVENTION

Compositions of matter provided by the present invention consist of and, preferably, consist essentially of recombinant human immune interferon isolates of high activity having a near-UV circular dichroic (CD) spectrum in aqueous solution at neutral pH with positive bands at about 259 nm, 266 nm, 280 nm, and 287 nm, and with shoulders at about 270 nm and 292 nm. Most preferable compositions of the invention are IFN-γ4A compositions which display characteristics as above in 0.1 molar ammonium acetate.

In practice of isolation procedures according to the present invention there are provided two predominant chromatographic interferon fractions, one spectrally characterized as above, and a second spectrally characterized as lacking any strong CD signals in the near-UV. The latter fraction may optionally be combined with the former (e.g., in weight ratios of 95:5, 90:10, 80:20, 70:30 and 60:40) to provide useful biologically active compositions or further processed to yield materials having the spectral characteristics of the former.

According to another aspect of the invention, there is provided a method for purifying recombinant human interferon which comprises the steps of purifying interferon in an aggregated form lacking intermolecular covalent bonds which is excluded from a Sephadex ™ G-75 column and unfolding the fraction in a solution containing a denaturant. The method further comprises the steps of diluting this solution to achieve a concentration of less than about 0.18 mg of interferon per milliliter and concentrating the diluted solution by diafiltration.

DETAILED DESCRIPTION

According to the present invention, recombinant human immune interferons, specifically IFN-γ4A, are purified using a technique of Sephadex ™ G-75 gel filtration in 1M urea and 0.1M ammonium acetate as a last step of the purification procedure. The amino acid sequence, and the base sequence of the synthetic gene from which it is derived, are given in Table I.

TABLE I

| | −1 | +1 | | | | | | | | | 10 | |
|---|---|---|---|---|---|---|---|---|---|---|---|---|
| | Met | Gln | Asp | Pro | Tyr | Val | Lys | Glu | Ala | Glu | Asn | Leu |
| | ATG | CAG | GAT | CCG | TAC | GTT | AAG | GAA | GCA | GAA | AAC | CTG |
| | TAC | GTC | CTA | GGC | ATG | CAA | TTC | CTT | CGT | CTT | TTG | GAC |

| | | | | | | | 20 | | | | | |
|---|---|---|---|---|---|---|---|---|---|---|---|---|
| Lys | Lys | Tyr | Phe | Asn | Ala | Gly | His | Ser | Asp | Val | Ala | Asp | Asn |
| AAA | AAA | TAC | TTC | AAC | GCA | GGC | CAC | TCC | GAC | GTA | GCT | GAT | AAC |
| TTT | TTT | ATG | AAG | TTG | CGT | CCG | GTG | AGG | CTG | CAT | CGA | CTA | TTG |

| | | | | 30 | | | | | | | | |
|---|---|---|---|---|---|---|---|---|---|---|---|---|
| Gly | Thr | Leu | Phe | Leu | Gly | Ile | Leu | Lys | Asn | Trp | Lys | Glu | Glu |
| GGC | ACC | CTG | TTC | CTG | GGT | ATC | CTG | AAA | AAC | TGG | AAA | GAG | GAA |
| CCG | TGG | GAC | AAG | GAC | CCA | TAG | GAC | TTT | TTG | ACC | TTT | CTC | CTT |

| 40 | | | | | | | | | 50 | | | |
|---|---|---|---|---|---|---|---|---|---|---|---|---|
| Ser | Asp | Arg | Lys | Ile | Met | Gln | Ser | Gln | Ile | Val | Ser | Phe | Tyr |
| TCC | GAC | CGT | AAG | ATC | ATG | CAG | TCT | CAA | ATT | GTA | AGC | TTC | TAC |
| AGG | CTG | GCA | TTC | TAG | TAC | GTC | AGA | GTT | TAA | CAT | TCG | AAG | ATG |

| | | | | | 60 | | | | | | | |
|---|---|---|---|---|---|---|---|---|---|---|---|---|
| Phe | Lys | Leu | Phe | Lys | Asn | Phe | Lys | Asp | Asp | Gln | Ser | Ile | Gln |
| TTC | AAA | CTG | TTC | AAG | AAC | TTC | AAA | GAC | GAT | CAA | TCC | ATC | CAG |
| AAG | TTT | GAC | AAG | TTC | TTG | AAG | TTT | CTG | CTA | GTT | AGG | TAG | GTC |

| | 70 | | | | | | | | | 80 | | |
|---|---|---|---|---|---|---|---|---|---|---|---|---|
| Lys | Ser | Val | Glu | Thr | Ile | Lys | Glu | Asp | Met | Asn | Val | Lys | Phe |
| AAG | AGC | GTA | GAA | ACT | ATT | AAG | GAG | GAC | ATG | AAC | GTA | AAA | TTC |
| TTC | TCG | CAT | CTT | TGA | TAA | TTC | CTC | CTG | TAC | TTG | CAT | TTT | AAG |

| | | | | | | | 90 | | | | | |
|---|---|---|---|---|---|---|---|---|---|---|---|---|
| Phe | Asn | Ser | Asn | Lys | Lys | Lys | Arg | Asp | Asp | Phe | Glu | Lys | Leu |
| TTT | AAC | AGC | AAC | AAG | AAG | AAA | CGC | GAT | GAC | TTC | GAG | AAA | CTG |
| AAA | TTG | TCG | TTG | TTC | TTC | TTT | GCG | CTA | CTG | AAG | CTC | TTT | GAC |

| | | | 100 | | | | | | | | | |
|---|---|---|---|---|---|---|---|---|---|---|---|---|
| Thr | Asn | Tyr | Ser | Val | Thr | Asp | Leu | Asn | Val | Gln | Arg | Lys | Ala |
| ACT | AAC | TAC | TCT | GTT | ACA | GAT | CTG | AAC | GTG | CAG | CGT | AAA | GCT |
| TGA | TTG | ATG | AGA | CAA | TGT | CTA | GAC | TTG | CAC | GTC | GCA | TTT | CGA |

| 110 | | | | | | | | | | 120 | | |
|---|---|---|---|---|---|---|---|---|---|---|---|---|
| Ile | His | Glu | Leu | Ile | Gln | Val | Met | Ala | Glu | Leu | Ser | Pro | Ala |
| ATT | CAC | GAA | CTG | ATC | CAA | GTT | ATG | GCT | GAA | CTG | TCT | CCT | GCG |
| TAA | GTG | CTT | GAC | TAG | GTT | CAA | TAC | CGA | CTT | GAC | AGA | GGA | CGC |

| | | | | | 130 | | | | | | | |
|---|---|---|---|---|---|---|---|---|---|---|---|---|
| Ala | Lys | Thr | Gly | Lys | Arg | Lys | Arg | Ser | Gln | Met | Leu | Phe | Arg |
| GCA | AAG | ACT | GGC | AAA | CGC | AAG | CGT | AGC | CAG | ATG | CTG | TTT | CGT |
| CGT | TTC | TGA | CCG | TTT | GCG | TTC | GCA | TCG | GTC | TAC | GAC | AAA | GCA |

| | 140 | | | | | | | | | | | |
|---|---|---|---|---|---|---|---|---|---|---|---|---|
| Gly | Arg | Arg | Ala | Ser | Gln | OP | | | | | | |
| GGT | CGC | CGT | GCT | TCT | CAG | TGA | TAGTCGAC | | | | | |
| CCA | GCG | GCA | CGA | AGA | GTC | ACT | ATCAGCTG | | | | | |

In this procedure, it is found that IFN-γ4A elutes as two peaks, one of which represents an associated state and the other of which may represent a monomer state. In the associated state, the protein solution in urea and ammonium acetate cannot ordinarily be enriched above about 1 mg/ml by ultrafiltration without resultant precipitation of product and the IFN-γ4A activity is found to be on the order of $0.5 \times 10^7$ to $2 \times 10^7$ units/mg.

By using the method according to the present invention, IFN-γ4A may be separated in each state and the putative monomer protein may be concentrated to greater than 5 mg/ml with as great an activity as $6 \times 10^7$ to $10 \times 10^7$ units/mg. The separated fraction of the associated proteins or the associated fraction alone may be virtually entirely converted to the monomer state by 7M urea treatment followed by gel filtration. The converted protein appears to be as soluble and as active as the isolated monomer protein. Conversion is desirable inasmuch as the activity of the associated state is only one-fourth to one-eighth as great as the activity associated with the monomer state.

The procedure for converting the associated state to the monomer state (referred to hereinafter as "peak I" and "peak II", respectively) involves completely unfolding the protein in the presence of 7M urea, followed by dilution into aqueous ammonium acetate and chromatography on a G-75 column in 1M urea.

The following examples illustrate the preparation and characterization of peak I and peak II IFN-γ4A according to the present invention. Example 1 describes isolation of IFN-γ4A from *E.coli* and the peak I and peak II material obtained thereby. Example 2 sets forth the characterization of peak I and peak II by means of circular dichroic spectra. Example 3 discusses the gel filtration analysis of IFN-γ4A. Example 4 examines the dependence of the outcome of refolding upon protein concentration. Example 5 describes the effect of the solvent used upon refolding. Example 6 examines the effect of various solvents upon the solubility of peak I and peak II. Example 7 discloses the determination of the sedimentation velocities of peak I and peak II. Example 8 describes the determination of the specific activities of peaks I and II. Example 9 illustrates the conversion of peak I material to peak II material.

EXAMPLE 1

The following procedure is a much preferred method which offers significant advantages for the isolation and purification of rIFN-γ.

Pelleted *E.coli* cells containing IFN-γ4A were dispersed with a suitable mixture, for example, a Polytron TM mixer, for about five minutes at room temperature. The resulting cell suspension was passed through a homogenizer four times at 7,000 psi, with cooling to about 11° C. between passes. The homogenate was centrifuged at 4200 rpm for about 45 minutes at 4° C. to produce a pellet.

The pellet was suspended in 2.6 l solubilization buffer per kg of starting cell paste (200 mM Tris-HCl, 7M urea, pH 9.0) at 5° C. and dispersed with a mixer for 15 minutes in an ice bath until a homogenous suspension was obtained. An amount of 10% polyethyleneimine (PEI) was added to 0.001 times the volume of the suspension, and the solution was and the solution was stirred for 15 minutes at 5° C. The suspension was then centrifuged at 4200 rpm for 40 minutes at 5° C.

The supernatant was decanted and the pH of the supernatant was adjusted to 8.1 at 5° C. using 2N HCl. The solution was diluted with 8M urea until the conductivity was less than or equal to 700 μS/cm.

One liter of Whatman SE-53 resin, equilibrated in a buffer (40 mM Tris-HCl, 6M urea, pH 8.1), was added per kilogram of starting cell paste and stirred gently for an hour at 5° C. To a funnel of suitable size, 500 ml of SE-53 resin (per kilogram of starting paste), previously equilibrated with SE-53 buffer, was added. A moist bed of resin was obtained using a vacuum pump and a suction filter by pouring 200-400 ml of SE-53 buffer into the funnel and filtering the slurry until a moist cake remained. To the washed resin, 2-3 l of SE-53 buffer at 5° C. were added and the resin was stirred to obtain an even gel slurry. The gel suspension was poured into a column and the flow rate was adjusted to 6-12 ml per minute. Fractions were collected in 0.2 column volume increments.

Elution of the IFN-γ4A was obtained using a linear gradient of 0M to 0.4M NaCl in buffer A (40 mM Tris-HCl, 6M urea, pH 8.1).

A column containing SE-53 resin which had been equilibrated with buffer (40 mM Tris-HCl, 6M urea, pH 9) was prepared and fractions containing greater than 70% IFN-γ4A from the previous step were loaded onto the column. The column was washed with 600 ml of buffer C (40 mM Tris-HCl, 6M urea, 30 mM NaCl, pH 9.0), and eluted with a linear gradient of from 30 mM to 330 mM NaCl. The flow rate was adjusted to 6-12 ml per minute.

Fractions containing greater than 85-90% IFN-γ4A were pooled and titrated to pH 7.5 using 2N HCl. The solution was brought to a concentration of 0.5M NaCl, and loaded onto a silica gel column. The column was eluted with a gel elution buffer (9% ethanol, 40 mM Tris-HCl, 6M urea, 0.5M NaCl, pH 7.5) with a linear gradient of 0-9% ethanol. Fractions eluted without ethanol and ethanol-eluted fractions which were free of high molecular weight contaminants were pooled.

The pool resulting from the previous step was concentrated to approximately 2 mg/ml using a Pellicon TM cassette with a 10,000 molecular weight cut-off membrane and equilibrated with G-75 buffer (0.1M ammonium acetate, 1M urea). The pool was then loaded onto a Sephadex TM G-75 column and eluted with G-75 buffer at a flow rate of 10-16 ml per minute. Forty-five fractions of 200 ml each were collected.

The IFN-γ4A obtained by the above procedures was better than 95% pure, based on SDS polyacrylamide gel electrophoretic analysis (coomassie blue and silver staining).

Proper folding of IFN-γ4A was attempted by adding solid urea to an approximately 1 mg/ml solution of the IFN-γ4A obtained from the above procedures, in 0.1M ammonium acetate to a final concentration of 7M, which fully unfolds the protein.

Upon dialysis, two structurally different forms, peak I and peak II, were obtained. Peak 2 was observed to be stable over a long period and was not observed to convert to the peak I form. On the other hand, an extremely slow conversion of peak I to peak II was observed in 0.1M ammonium acetate and this conversion may be accelerated in the presence of 1M urea or at lower ionic strength.

EXAMPLE 2

Circular dichroic spectra were determined at room temperature on a Jasco J-500C spectropolarimeter as available from Jasco, Tokyo, Japan. Spectral band width was set at 1 nm and cuvettes used were 0.1 and 1 cm in light pass length for 190-260 nm and 240-340 nm, respectively. For each sample, the solvent spectrum was obtained and subtracted from the protein spectrum. The mean residue ellipticity, [θ], was calculated from the mean residue weight (117) for IFN-γ4A.

Figure 1:
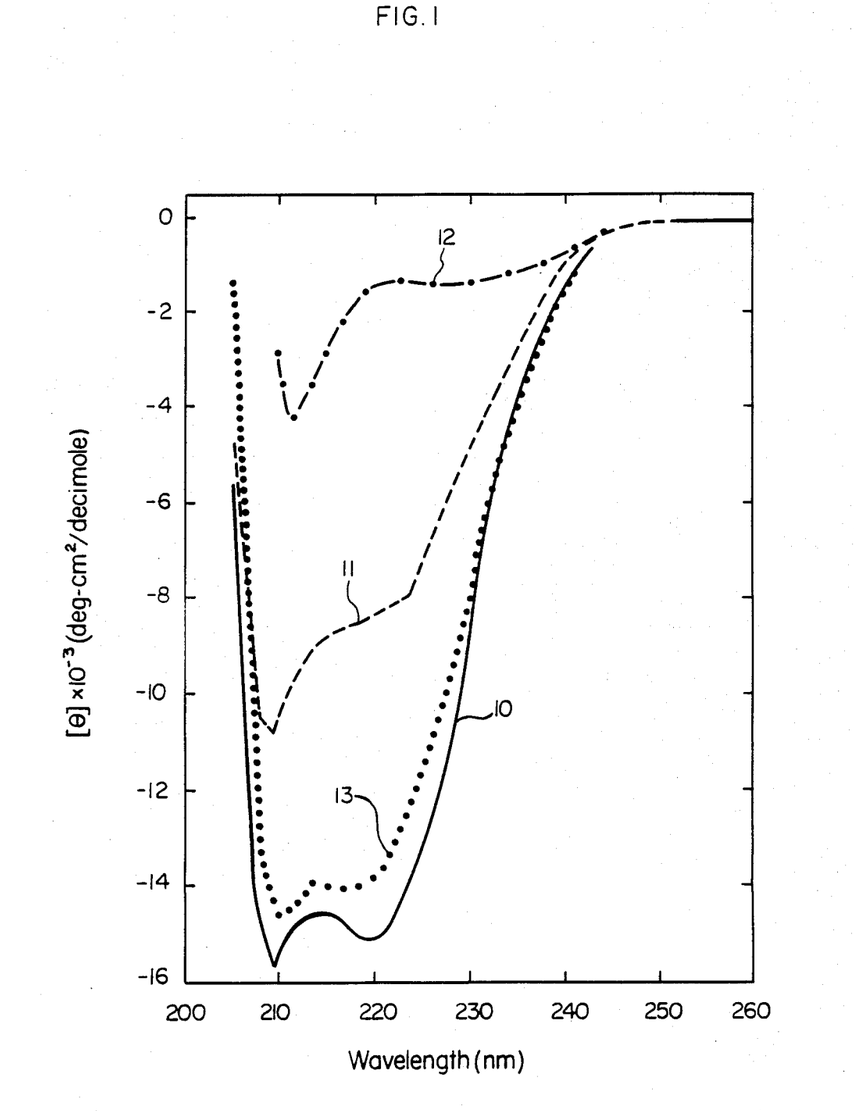
FIG. 1 illustrates the far-UV circular dichroic spectra of IFN-γ4A under different conditions.

FIG. 1 shows the far-UV circular dichroic spectrum of peak II in 0.1M ammonium acetate as line 10. The spectrum is characterized by two minima, at 209 and 220 nm, indicating the presence of ordered structures. 1 mg/ml of peak II in 0.1M ammonium acetate was dialyzed against a pH 2 buffer and the circular dichroic spectrum is shown in FIG. 1 as curve 11. This spectrum shows a minimum at 209 nm and a shoulder around 216 nm, displaying a substantial decrease in ellipticity over the wave length examined relative to the values in curve 10.

These changes in the circular dichroic spectrum indicate that IFN-γ4A is unfolded in acid at pH 2. On the other hand, the peak II spectrum in 7M urea, curve 12, shows little presence of ordered structures. It may therefore be concluded, that the ordered structures, such as α-helix and β-sheet, still exist in acid, although these structures, in particular α-helix, are significantly lost in acid compared with a native state. Thus, the unfolding of IFN-γ4A in acid is partial relative to the unfolding which occurs in 7M urea.

The acid-unfolded sample was dialyzed against 0.1M ammonium acetate to renature the protein. The far-UV circular dichroic spectrum of the product is shown in FIG. 1 as curve 13. Curve 13 indicates that IFN-γ4A, partially unfolded in acid, was refolded into a structure similar to the initial peak II material, although small differences exist before and after acid treatment in the magnitude of ellipticity and peak positions.

Figure 2:
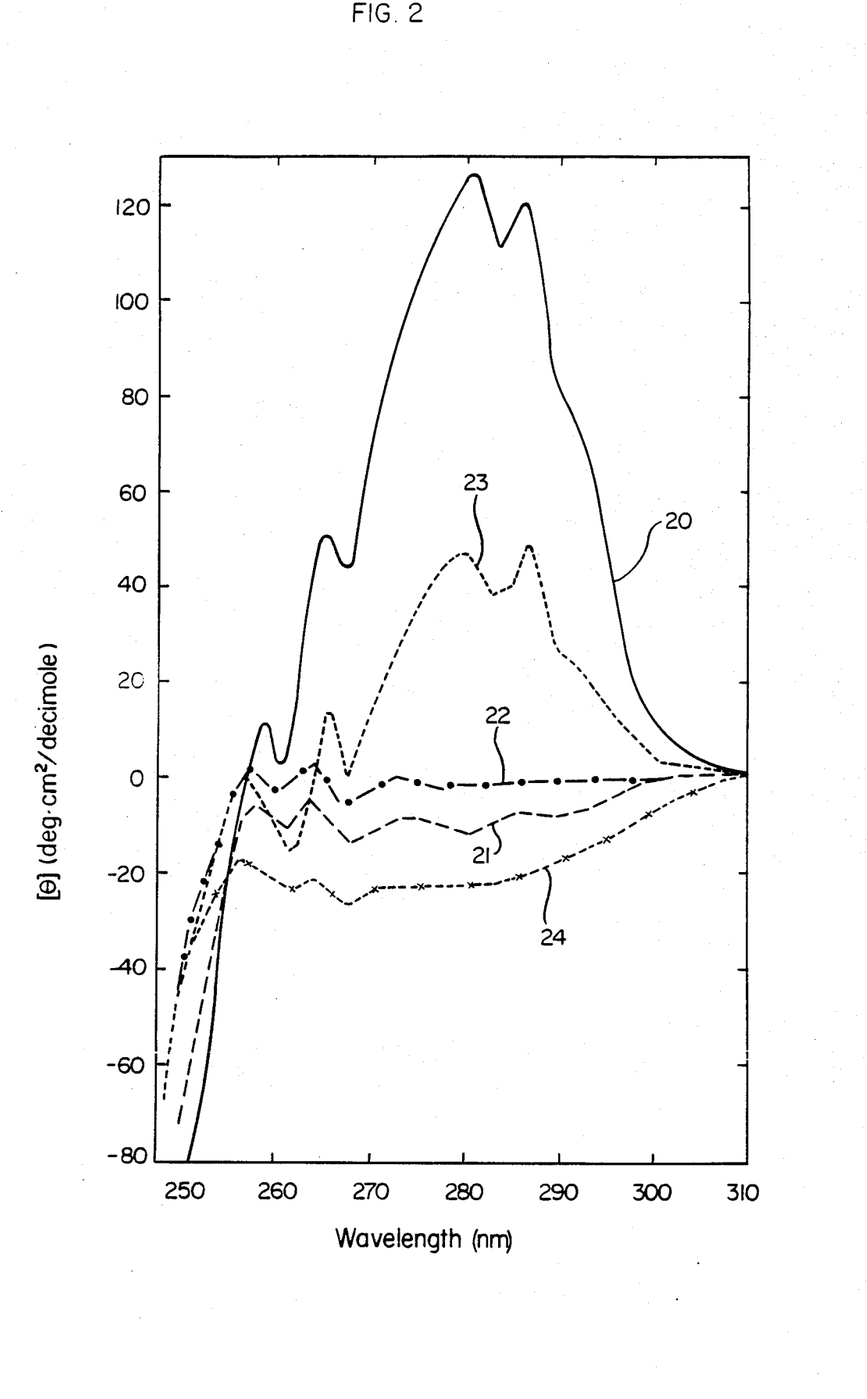
FIG. 2 shows the near-UV circular dichroic spectra of IFN-γ4A under different conditions.

Near-UV circular dichroic spectra are respectively shown in curves 20, 21, 22, and 23 of FIG. 2. The native peak peak II in 0.1M ammonium acetate is characterized by several positive peaks and shoulders in curve 20. This suggests that aromatic residues are incorporated into a rigid tertiary structure in peak II which provides asymmetric environments for those residues to give rise to aromatic circular dichroic signals. The spectrum of IFN-γ4A in acid, as shown by curve 21, is entirely different from the native spectrum and exhibits little distinct circular dichroic signals in the near-UV region, similar to the spectrum of IFN-γ4A unfolded in 7M urea of curve 22. Thus, when peak II is dialyzed against acid, it appears to lose its rigid tertiary structure, although the secondary structure is apparently only partially unfolded.

The near-UV circular dichroic spectrum of peak II in 0.1M ammonium acetate after acid treatment, curve 23, is intermediate between the native peak II (curve 20) and acid-unfolded (curve 21) structures. This result is in contrast to the far-UV circular dichroic result for the same sample, which suggests almost complete recovery to the native spectrum. Therefore, it is suggested that the acid-unfolded IFN-γ4A may refold into a secondary structure similar to peak II but that the tertiary structure may be only partially restored. Alternatively, it is possible that the refolding results in formation of both peak I and peak II and that the observed near-UV circular dichroic spectrum is the average of the spectra of the two forms. An indication in support of this latter hypothesis is given in curve 24 of FIG. 2, which shows that peak I gives small negative circular dichroic signals.

EXAMPLE 3

Analytical gel filtration was performed on a Sephadex ™ G-75 column (1×120 cm) in 0.1M ammonium acetate containing 1M urea at pH 7 and at 4° C.

Figure 3:
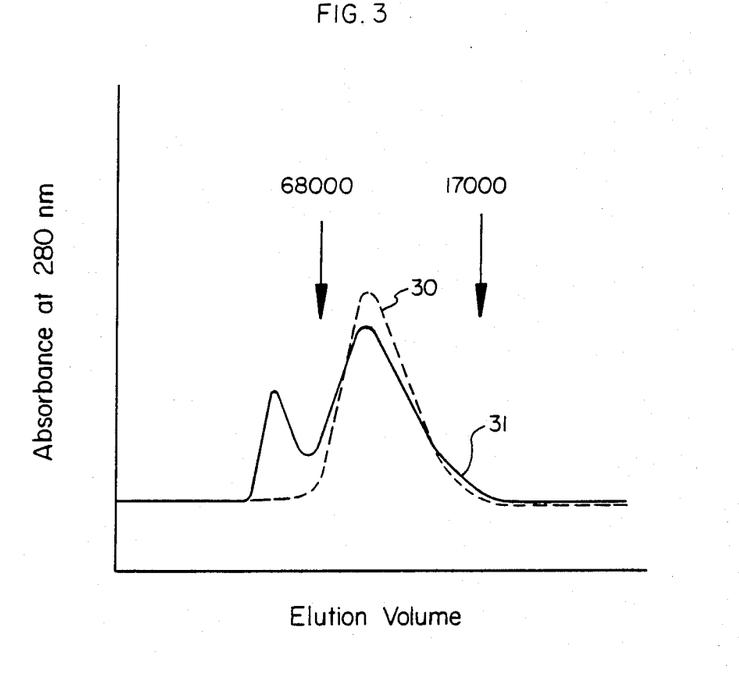
FIG. 3 is a graph of a gel filtration analysis of IFN-γ4A under different conditions.

Formation of two forms (peak I and peak II) after refolding of acid-treated peak II was confirmed by analytical gel filtration, as shown in FIG. 3. Native peak II eluted between bovine serum albumin (68,000 molecular weight) and myoglobin (17,000 molecular weight) in a single peak, curve 30. Acid treatment of the peak II sample gave rise to two peaks, curve 31, one being at the void volume and the other at the same elution position as the native peak II. The percentage of peak II formed was 75% under these conditions, which agrees qualitatively with the observed intermediate values of ellipticity in the near-UV region for the refolded sample. The above results are similar to the results observed when IFN-γ4A in the peak II form was unfolded in 7M urea and refolded by lower urea concentration.

It has been consistently observed that peak I is 4- to 8-fold less active than peak II. Thus, generation of peak I from peak II should yield a drop in the specific activity of IFN-γ4A.

EXAMPLE 4

The dependence of the outcome of refolding upon protein concentration was examined. Peak II solution at 0.5 to 4 mg/ml in 0.1M ammonium acetate were treated as described above and analyzed by near-UV and second derivative spectra and gel filtration. Protein concentration was determined spectrophotometrically in 3M guanidine hydrochloride using the extinction coefficient of 0.65 ml/(mg, cm) at 280 nm.

Figure 4:
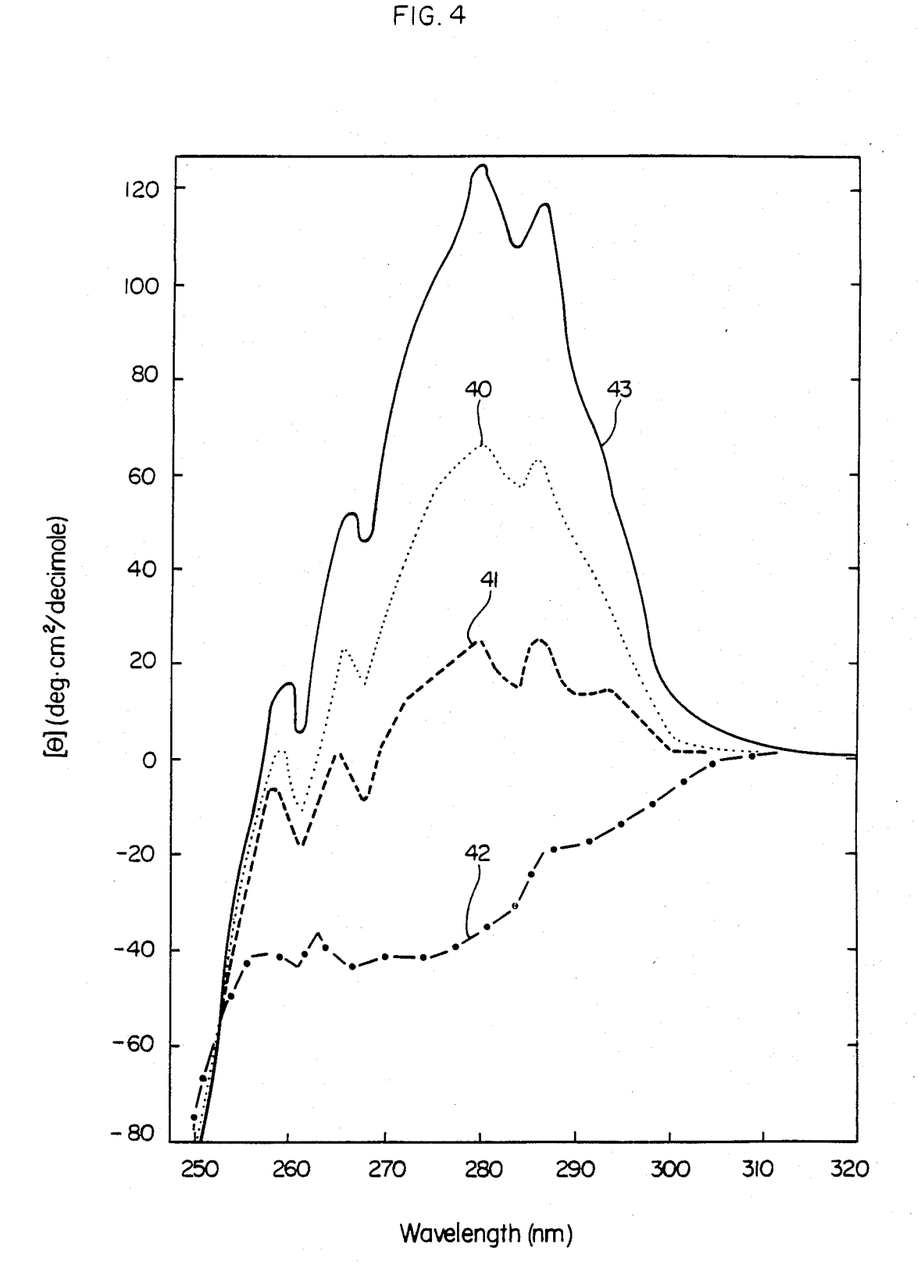
FIG. 4 shows the near-UV circular dichroic spectra of IFN-γ4A under different conditions.

For the studies of protein concentration dependence, the circular dichroic spectra are shown in FIG. 4 and the results are summarized in Table II.

TABLE II

| Protein Concentration mg/ml | Appearance[a] | Peak II Formed (%) | [θ] at 280 nm $\frac{deg \cdot cm^2}{decimole}$ |
|---|---|---|---|
| 0.5[b] | clear | 100 | 125 |
| 0.5 | clear | 80 | 66 |
| 1 | clear | 56 | 24 |
| 2 | clear | 28 | −36 |
| 4 | precipitation[c] | — | — |

[a]Appearance of the solution after acid treatment
[b]Untreated peak II
[c]After centrifugation, no protein was oberved in the supernatant The 4 mg/ml sample showed extensive precipitation after dialysis back to 0.1M ammonium acetate, although the solution was clear at pH 2. This indicates that the aggregation resulting in precipitation occurs when the protein was refolded from acid. This sample was centrifuged and a protein concentration determination of the supernatant indicated that all of the protein had precipitated.

The samples of 0.5 mg/ml, 1 mg/ml, and 2 mg/ml are respectively shown in FIG. 4 as curves 40, 41, and 42. These circular dichroic spectra are different from the spectrum for the native peak II, shown as curve 43 in FIG. 4, and depend upon the protein concentration. The 2 mg/ml sample gave a spectrum similar to that observed for a typical peak I preparation. The gradual change in ellipticity with protein concentration is set forth in Table II as a change in the [θ] at 280 nm.

Figure 5:
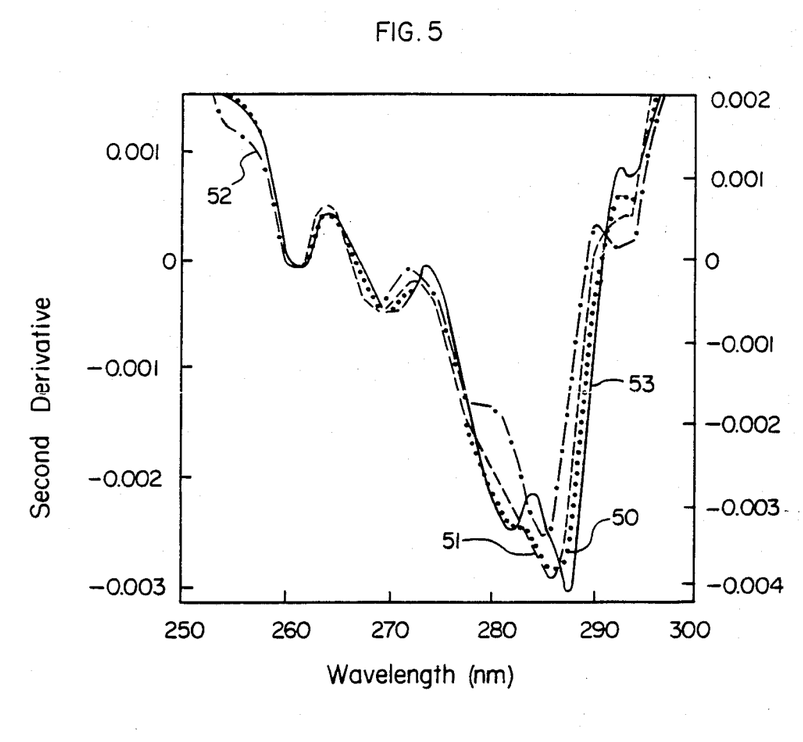
FIG. 5 depicts the second derivative spectra of IFN-γ4A under different conditions.

The second derivative spectra of UV absorbance for these samples were measured after adjusting the protein concentrations to about 0.5 mg/ml and are, respectively, shown in FIG. 5 as curves 50, 51, 52, and 53. The second derivative spectrum has been shown to be sensitive to alterations in protein structure. Ishikawa, et al., *Biochim.Biophys.Acta*, 580: 120-128 (1979).

The native peak II spectrum, curve 53, is characterized by a positive peak at 292 nm and negative peaks at 282 and 287.5 nm in a range from 270-300 nm.

The spectrum after acid treatment at 2 mg/ml showed marked differences from the native spectrum: a positive peak at 290 nm, a negative peak at 285 nm, and a negative shoulder at around 275 nm. These characteristics are typical for peak I. The acid-treated samples at 0.5 and 1 mg/ml showed an intermediate pattern between the native peak II and the 2 mg/ml sample. These circular dichroic and UV absorbance results suggest that the acid treatment of peak II leads to formation of peak I and that the extent of peak I formation depends upon the protein concentration.

Table II summarizes results of analytical gel filtration for the acid-treated and native peak II samples. The results for the native peak II show that no proteins were detected within the limits of detection at the elution position for peak I. The acid-treated samples showed presence of both peak I and peak II forms. Higher protein concentration promoted greater formation of peak I. Because formation of peak I is due to aggregation of the protein, the complete precipitation which occurred at 4 mg/ml may be due to extremely enhanced formation of peak I aggregates large enough to precipitate. These results confirm the circular dichroic and UV absorbance results in that greater formation of peak I occurs when peak II is subjected to the acid treatment at higher protein concentrations. The result at 1 mg/ml (Table I) shows a 44% formation of peak I, as opposed to 25% formation in the previous case, suggesting that peak I formation depends slightly on the exact procedure for unfolding and refolding.

EXAMPLE 5

Solvent effect on refolding

IFN-γ4A was refolded in 5 mM phosphate (pH 7) and 0.01M and 0.1M ammonium acetate. The results of gel filtration and circular dichroic analyses are summarized in Table III.

the total protein was precipitated and the protein remaining in the supernatant was in the peak II form as determined by analytical gel filtration.

It was also observed that when 40 mM phosphate (pH 7) was used for refolding, the sample at 0.5 mg/ml showed about 20% of protein in the precipitate and the soluble fraction was in the peak II form (data not shown). These results are similar to those for 5 mM phosphate, although higher phosphate concentrations appear to be more effective in causing protein precipitation.

At a protein concentration of 0.5 mg/ml, both 5 mM phosphate and 0.01M ammonium acetate showed 100% formation of peak II. Less peak II was formed in 0.1M ammonium acetate, as demonstrated by analytical gel filtration and circular dichroic spectra. This tendency was also observed at a protein concentration of 2 mg/ml, although 5 mM phosphate caused a precipitation as described above. These results clearly indicate that lower ionic strength (i.e., 5 mM phosphate and 0.01M ammonium acetate relative to 0.1M ammonium acetate) favors the formation of peak II.

A comparison of the results at a protein concentration of 2 mg/ml between 5 mM phosphate and 0.01M ammonium acetate suggests that the former solvent also resulted in formation of peak I in the form of precipitation as observed. If this is correct, peak II formation in 5 mM phosphate, when IFN-γ4A at 2 mg/ml was used, is 73%, which is slightly smaller than that observed for 0.01M ammonium acetate. This suggests a similarity between 5 mM phosphate and 0.01M ammonium acetate in ability to form peak II. The result observed at 2 mg/ml in 0.1M ammonium acetate (47% peak II formation) is slightly different from the previous result for the same conditions (Table II, 28% peak II formation) and this difference again suggests that IFN-γ4A refolding may vary sightly depending on exact unfolding and refolding conditions.

EXAMPLE 6

Solvent Effect on the Solubility of Peak I and Peak II

The above results indicated that the refolding of IFN-γ4A after acid treatment depends on the solvent systems and that phosphate buffer causes a precipitation. Therefore, the potential for peak I precipitation was studied by dialyzing a peak I preparation in 0.1M ammonium acetate which contained 20% peak II, against

TABLE III

| Protein Concentration mg/ml | Solvent for Refolding | Appearance[a] | Peak II Formed[a] % | [θ] at 280 nm deg · cm² decimole |
|---|---|---|---|---|
| 0.5 | 5 mM phosphate (pH 7) | clear | 100 | 126 |
| 2 | 5 mM phosphate (pH 7) | precipitation[b] | 100[c] | — |
| 0.5 | 0.01 M ammonium acetate | clear | 100 | 124 |
| 2 | 0.01 M ammonium acetate | clear | 90 | 109 |
| 0.5 | 0.1 M ammonium acetate | clear | 85 | 92 |
| 2 | 0.1 M ammonium acetate | clear | 47 | 7 |

[a]Percentage of peak II in the total eluted protein.
[b]After centrifugation, 73% of starting material was found in the supernatant.
[c]The value is obtained by analyzing the supernatant on analytical gel filtration.

None of the solutions studied, except for the 2 mg/ml sample in 5 mM phosphate (pH 7), showed precipitation after acid treatment. For the 2 mg/ml sample, 27% of various solvents. The results, given in Table IV, showed that nearly 80% of protein precipitated for all the phosphate buffers examined while no precipitation occurred in aqueous ammonium acetate. Gel filtration analysis and the second derivative spectrum for the phosphate buffer samples indicated that the protein in the supernatant, which is approximately 20% of the total, is in the peak II form. This percentage is identical to that present in the starting material and suggests that the phsophate buffers did not affect the ratio of peak I and peak II in the sample but led to complete precipitation of peak I.

The results shown in Table IV also indicate that about 80% of the IFN-γ4A remained as peak I when dialyzed against 0.1M ammonium acetate. This agrees with the previous observation that formation of peak II from peak I is not significant in 0.1M ammonium acetate, although it was observed to occur very slowly. The last column of Table IV shows percentages of peak II observed in these solvents. Except for 0.01M ammonium acetate, these percentages are constant at about 20%, and are thus identical to the amount of peak II present in the starting material. The results suggest that these solvents are identical in that they do not alter the peak I to peak II ratio but are different in that the phosphate buffers lead to peak I precipitation while 0.1M ammonium acetate has no such effect.

TABLE IV

| Solvent | Appearance | Protein in Supernatant % | % of Peak II in Supernatant[a] | % of Peak II in the Total |
|---|---|---|---|---|
| 5 mM phosphate (pH 7) | clouded | 20 | 100 | 20 |
| 40 mM phosphate (pH 7) | precipitation | 20 | 100 | 20 |
| PBS[b] | percipitation | 15 | 100 | 15 |
| 0.01 M ammonium acetate | clear | 100 | 55 | 55 |
| 0.1 M ammonium acetate | clear | 100 | 20 | 20 |

[a]Determined by analytical gel filtration
[b]5 mM phosphate (pH 7) containing 0.15 M NaCl The result for 0.01M ammonium acetate showed a difference from that for other solvents. It increased the amount of peak II in the sample during dialysis from 20% (starting material) to 55%, as determined by analytical gel filtration. This result agrees with the previous observation that low ionic strength enhances the disaggregation of peak I and, hence, peak II formation.

On the other hand, when peak II at 0.5 to 2 mg/ml was treated in the same way, it showed no precipitation in any of the solvent systems (not shown). Peak II maintained its size and structure for all cases, as determined by analytical gel filtration and second derivative spectrum analysis (not shown).

It appeared that the solubility of peak I depends on the kind of ionic species present in the solvents. Therefore, other solvent systems were tested, such as 5 mM Tris-borate buffer (pH 7.5), 0.1M ammonium acetate containing 5 mM $CaCl_2$, 5 mM carbonate (pH 7.5) titrated with HCl and 0.01M ammonium acetate containing 5 mM $Na_2SO_4$ (pH 7.0). None of these solvents, except for 0.01M ammonium acetate containing 5 mM $Na_2SO_4$, caused precipitation.

At the pH used, borate and carbonate exist mainly as monovalent ion, suggesting that the monovalent anions in general do not cause peak I precipitation. The divalent cation, $Ca^{2+}$, also did not have such effect. The $Na_2SO_4$-containing solvent brought about 85% precipitation, equivalent to the amount of peak I present in the starting material.

A similar result is obtained when phosphate buffers are used. Since this solvent and phosphate buffers contain divalent anions and IFN-γ4A has a very high isoelectric point, the results suggest that divalent anions may act as a cross-linker for positively charged IFN-γ4A and may facilitate additional bonds between peak I molecules which are already aggregating. Because 5 mM phosphate, or 0.01M ammonium acetate containing 5 mM $Na_2SO_4$, have low ionic strength, they might be expected to enhance formation of peak II, which is contrary to the observations. It is possible that the cross-linking effect of divalent anions overwhelms the disaggregation effect of the solvents due to low ionic strength.

EXAMPLE 7

Sedimentation velocity experiments were carried out using a Spinco Model E ultracentrifuge equipped with Schlieren optics and a temperature control unit. An aluminum-filled epon double-sector centerpiece with quartz windows was employed. All runs were performed at 25° C.

A fast sedimenting peak, possibly corresponding to peak I, gave a sedimentation constant of approximately 20 S in 0.1M ammonium acetate at 2 to 5 mg/ml. A slow sedimenting peak, possibly peak II, gave a sedimentation constant of approximately 2.8 S when extrapolated to zero protein concentration. It appears that the ratio of the two sedimentation peaks in the sample is independent of protein concentration, indicating that the two forms are not in a rapid reversible self-association.

EXAMPLE 8

The antiviral activity of IFN-γ4A preparations were examined with a standard cytopathic effect assay. HeLa cells were treated with the above-purified IFN-γ4A preparations or a standard and then challenged with Encephalomyocardis virus. The standard was a natural IFN-γ preparation, as available from Interferon Sciences, Inc., calibrated against the NIH standard (Gg-23-902-530). For comparison purposes, peak I and peak II materials were always assayed at the same time. The purified IFN-γ4A preparations were stored in 0.1M ammonium acetate, pH 6.9, at 4° C.

At the same dilution, peak II had two- to three-fold higher titers than peak I; i.e., peak II appears to be 4- to 8-fold more active, taking the protein concentration into account. This magnitude of difference between peak I and peak II was consistently observed for different preparations.

The range of specific antiviral activity observed for peak I was $0.5-2\times 10^7$ U/mg. For peak II, the range of observed antiviral activity was $6-10\times 10^7$ U/mg.

EXAMPLE 9

Unfolding and Refolding of Peak I

The results described above revealed that formation of peak I materials occurs when peak II is unfolded by acid and refolded by increasing the pH to neutral. Due to the higher activity of peak II, it is desirable to examine whether peak II formation may be promoted when peak I is used as starting material.

Figure 6:
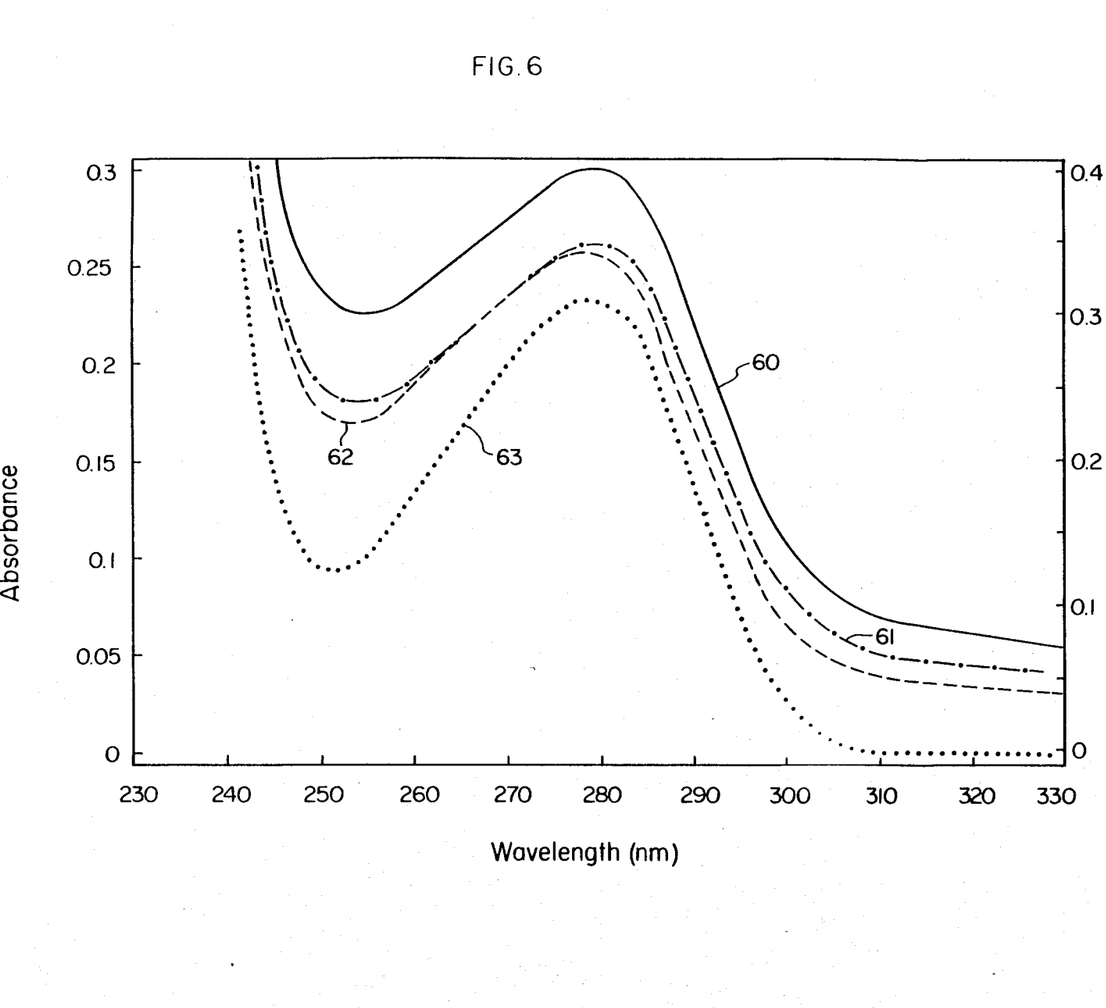
FIG. 6 illustrates the UV absorbance spectra of IFN-γ4A under different conditions.
Figure 7:
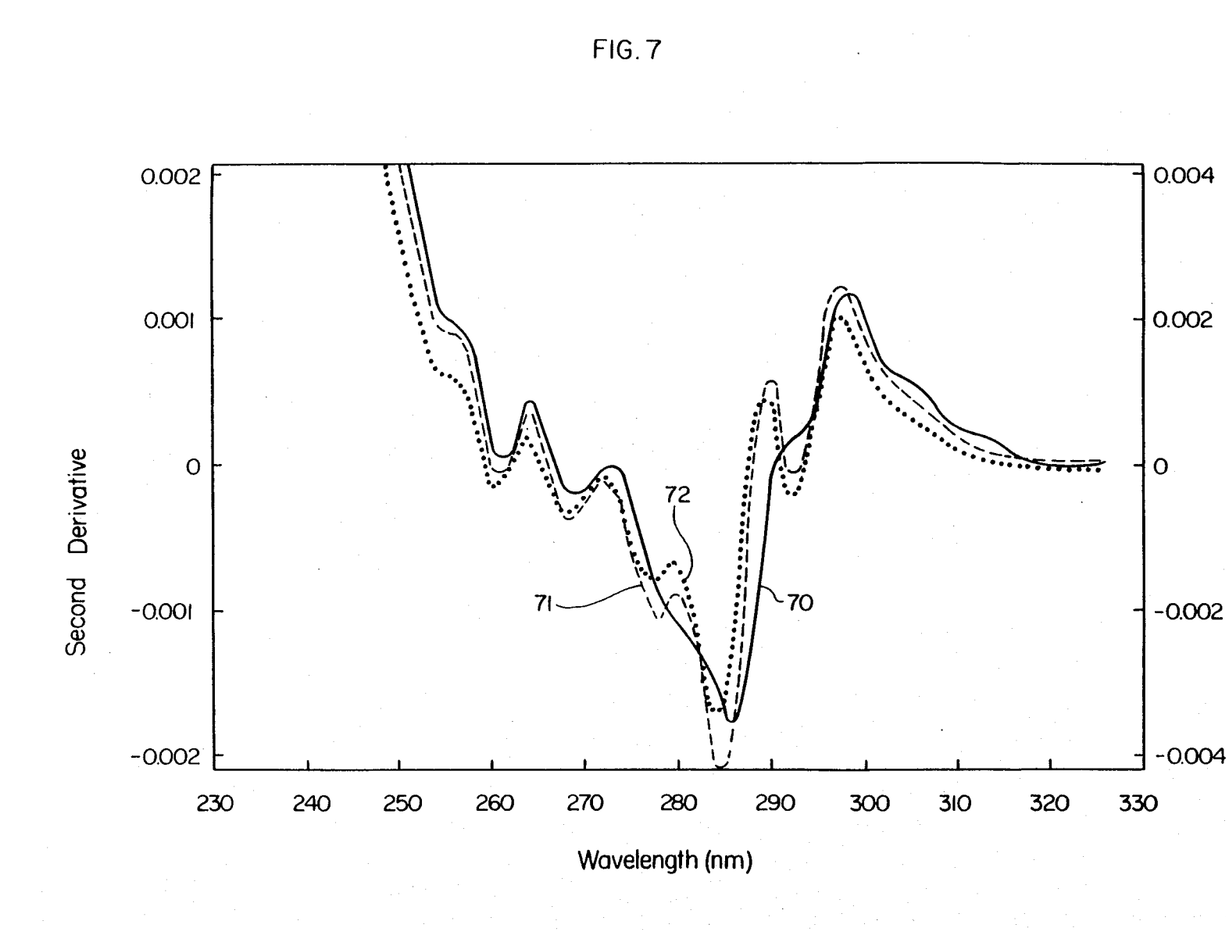
FIG. 7 illustrates the second derivative spectra of IFN-γ4A under different conditions.

The UV absorbance spectrum of a peak I preparation in 0.1M ammonium acetate (0.3 mg/ml), as shown in FIG. 6, curve 60, shows large light scattering, demonstrating that the sample is heavily aggregated. The second derivative of curve 60, as shown in FIG. 7, curve 70, displays a spectrum similar to that of a mixture of peak I and peak II. In fact, gel filtration analysis indicated the presence of 40% peak II in this peak I preparation. This peak I sample was dialyzed against acid and then 0.01M ammonium acetate. Since peak II formation from peak I occurs much faster in 0.01M than 0.1M ammonium acetate, circular dichroic and gel filtration experiments were carried out immediately after overnight dialysis against 0.01M ammonium acetate.

The UV absorbance spectrum of peak I in 0.01M ammonium acetate after acid treatment is shown in FIG. 6 as curve 61, to exhibit the sort of light scattering found for the starting material. The second derivative spectrum was identical within experimental error to the original peak I spectrum. These results indicate no changes in the tertiary structure and aggregation state before and after acid treatment of the peak I sample, as confirmed by gel filtration analysis. This indicates that the acid treatment has no effect on the ratio of peak I and peak II and that 0.01M ammonium acetate did not cause significant formation of peak II from peak I during dialysis against this buffer after acid treatment.

If the treatment can lead to the same state of unfolding regardless of whether peak I or peak II was used as starting material, one would expect 100% peak II formation at such low protein concentration (0.3 mg/ml) using 0.01M ammonium acetate as refolding solvent. Therefore, the structures of peak I and peak II at pH 2 were compared by UV absorbance and second derivative spectra. The second derivative spectra (FIG. 7) are very similar for peak I, shown as curve 71, and for peak II, shown as curve 72, indicating that the acid can similarly unfold the tertiary structure of both peak I and peak II. However, their UV absorbance spectra, as shown in FIG. 6, curve 62, for peak I and as shown in FIG. 6, curve 63 for peak II, are very different. Peak II shows no scattering in acid, while peak I still has large light scattering. This suggests that although acid can unfold peak I to the same extent as peak II, it cannot disaggregate peak I. Thus, the peak I form present in the starting sample maintained its aggregation state in acid and reformed the same structure upon removal of acid and the peak II form in the starting sample (which is approximately 0.12 mg/ml) was unfolded in acid and refolded into peak II. Thus, no change in the peak II to peak I ratio could occur by acid treatment.

Chromatographically purified peak I or peak II, or their mixture, was unfolded in 0.1M ammonium acetate, 7M urea and then refolded under various conditions. Because 7M urea can unfold the protein whether it is in the peak I or peak II form, the outcome was independent of which sample was used. Only results using Peak I as a starting material are, therefore, given. The results are shown in Table V.

TABLE V

| Experiment | Exchange Solvent[a] | Method of Exchange | Protein Concentration mg/ml | Peak II Formed % | Spectral Characteristic |
|---|---|---|---|---|---|
| 1 | 0.1 M | dialysis | 2 | 0 (approx.) | peak I |
| 2 | 0.1 M | dialysis | 1 | 50% | Mix |
| 3 | 0.1 M | dilution (25 ×) | 1 | 80% | Mix |
| 4 | 0.1 M | dilution (60 ×) | 1 | 95% (approx) | peak II |
| 5 | 0.01 M | dilution (5 ×) | 1 | 98% | peak II |
| 6 | 0.01 M | dilution (10 ×) | 1 | 100% | peak II |

[a]Peak I was made 0.1 M in ammonium acetate, 7 M in urea, and then dialyzed against or diluted with aqueous ammonium acetate. The buffer used for solvent exchange was ammonium acetate, at the contration listed.

The peak I protein in 0.1M ammonium acetate and 1M urea, at the concentration given in Table V, was made 7M in urea by adding solid urea, was allowed to stand for 2 hours, and was subjected to dialysis or dilution to lower urea concentration. Comparing experiments 1 and 2, it is evident that the lower protein concentration favors formation of peak II. This property is manifested in experiments 3 and 4, for which the protein concentration was also lowered by dilution. As shown in experiment 4, however, a greater than 95% formation of peak II required that the protein concentration be lowered to approximately 0.015 mg/ml if the solvent for dilution is 0.1M ammonium acetate. On the other hand, experiment 5 (for a dilution of interferon corresponding to about 0.18 mg/ml) and experiment 6 showed almost 100% formation of peak II at five- or ten-fold dilution when 10 mM ammonium acetate was used, these dilution factors being much smaller than those used for 0.1M ammonium acetate. It is therefore concluded that decreasing the ionic strength of the exchanging solvent favors the peak II formation.

While the present invention has been described in terms of a preferred embodiment, modifications and variations are expected to occur to those skilled in the art upon consideration of the foregoing illustrative embodiments of the present invention.

For example, the mechanism of acid instability of natural IFN-γ may be inferred from the results obtained with recombinant IFN-γ4A. If one assumes that the natural protein behaves in the same way as the recombinant protein, then the natural protein may yield both peak I-like and peak II-like forms after acid treatment, even though the starting sample may have contained only a peak II-like form. The presence of high molecular weight impurities may enhance the formation of a peak I-like form, for example, due to the excluded volume effect which would enhance protein aggregation. Minton, *Biopolymers,* 20: 2093–2120 (1981); Lee, et al., *Biochemistry,* 18: 5518–5526 (1979). It has been consistently observed that peak II is four to eight times more active than peak I in a standard CPE assay. Therefore, formation of peak I should lead to a decrease in the antiviral activity. When phosphate buffer was used as a refolding solvent, the decrease in the activity would be greater, since phosphate buffer was shown to precipitate peak I and such precipitation should lead to a complete loss of biological activity for peak I. It cannot be excluded, however, that the natural IFN-γ behaves differently from the recombinant protein due to such factors as glycosylation, different isoelectric points, and C-terminal processing.

Furthermore, in any form of interferon wherein formation of intermolecular disulfide bonds might occur (such as "mature" rIFN-γ), a reducing agent, such as dithiothreitol, may be added in the unfolding and diluting steps to prevent formation of such bonds.

As previously indicated, it is within the contemplation of the invention to "convert" peak I materials to peak II constitution. It is also contemplated that quite useful compositions may be provided through admixture or co-collection of peak II and peak I fractions in weight ratios of, for example, about 95:5, 90:10, 80:20, 70:30, or 60:40.

Consequently, it is intended that the present invention include all such equivalent variations which come within the scope of the invention as claimed.

What is claimed is:

1. A method for obtaining monomeric gamma interferon substantially free of associated states comprising the steps of:

providing purified gamma interferon in an aggregated form which lacks intermolecular covalent bonds and which is excluded from a gel filtration column whose characteristics are such that proteins of molecular weight greater than about 80,000 daltons are excluded;

unfolding the gamma interferon in a solution containing a denaturant;

diluting the solution to achieve a concentration of less than 0.18 mg of gamma interferon per ml; and concentrating the diluted solution by diafiltration.

2. The method as recited in claim 1 further comprising the step of reducing the ionic strength of the solution containing the denaturant.

* * * * *